United States Patent [19]

Walkup et al.

[11] Patent Number: 4,980,463
[45] Date of Patent: Dec. 25, 1990

[54] SUCROSE-6-ESTER CHLORINATION

[75] Inventors: Robert E. Walkup, Watkinsville; Juan L. Navia; Nicholas M. Vernon, both of Athens, all of Ga.

[73] Assignee: Noramco, Inc., Atlanta, Ga.

[21] Appl. No.: 382,147

[22] Filed: Jul. 18, 1989

[51] Int. Cl.$^5$ .................... C07H 1/00; C07H 13/00; C07G 3/00

[52] U.S. Cl. .................... 536/124; 536/122; 536/119; 536/115; 536/120; 536/4.1

[58] Field of Search ............... 536/124, 122, 119, 115, 536/120, 4.1

[56] References Cited

U.S. PATENT DOCUMENTS

| | | | |
|---|---|---|---|
| 4,262,115 | 4/1981 | Khan et al. | 536/122 |
| 4,291,158 | 9/1981 | Luteri | 536/122 |
| 4,324,888 | 4/1982 | Rathbone | 536/122 |
| 4,345,933 | 8/1982 | Luteri | 536/119 |
| 4,362,869 | 12/1982 | Jenner et al. | 536/122 |
| 4,380,476 | 4/1983 | Mufti et al. | 536/122 |
| 4,549,013 | 10/1985 | Hough et al. | 536/122 |
| 4,612,373 | 9/1986 | Khan et al. | 536/122 |
| 4,617,269 | 10/1986 | Rathbone et al. | 435/97 |

OTHER PUBLICATIONS

Walter A. Szarek, "Deoxyhalogeno Sugars", in *Advances in Carbohydrate Chemistry & Biochemistry*, 28, 230–259 (1973).
Viehe et al., "The Chemistry of Dichloromethylene-Ammonium Salts" ('Phosgenimonium Salts'), *Angew Chem. Internat. Edit.*, 12 (10), 806–818 (1973).
Hanessian et al., "A New Synethesis of Chlorodeoxy-Sugars", *Chem. Commun.*, 1967, 1152–1155.
R. L. Whistler and A. K. M. Anisuzzaman in "Methods in Carbohydrate Chemistry", vol. VIII, R. L. Whistler and J. N. BeMiller, Eds., Academic Press, New York, 1980, pp. 227–231.
Eilingsfeld et al., *Angew. Chem,* 72 (22), 836–845 (1960).
L. Hough, S. P. Phadnis, and E. Tarelli, *Carbohydr. Res.*, 44, 35 (1975).
J. E. G. Barnett, *Adv. Carbohydr. Chem.*, 22, 177 (1967).
R. A. Khan, *Adv. Carbohydr. Chem. Biochem.*, 33, 235 (1976).
M. R. Jenner in "Developments in Food Carbohydrates-2", C. K. Lee, Ed., Applied Science, London, 1980, pp. 91–143.

Primary Examiner—Ronald W. Griffin
Assistant Examiner—Everett White
Attorney, Agent, or Firm—Charles J. Metz

[57] ABSTRACT

A process for the chlorination of sucrose-6-esters to produce 6',4,1'-trichlorosucrose-6-esters which comprises the steps of:
(a) adding at least seven molar equivalents of an acid chloride to a reaction mixture containing a sucrose-6-ester and a tertiary amide to form initially a chloroformiminium chloride salt which subsequently forms a complex with the hydroxyl groups of the sucrose-6-ester;
(b) subjecting the reaction mixture product of step (a) to an elevated temperature not higher than about 85° C. for a period of time sufficient to produce a mixture of chlorinated sucrose-6-ester products consisting essentially of 6'-chlorosucrose-6-ester, 4,6'-dichlorosucrose-6-ester, and 1',6'-dichlorosucrose-6-ester; and
(c) subjecting the reaction mixture product of step (b) to an elevated temperature not higher than about 125° C. for a period of time sufficient to produce a chlorinated product consisting essentially of 1',4,6'-trichlorosucrose-6-ester.

24 Claims, 6 Drawing Sheets

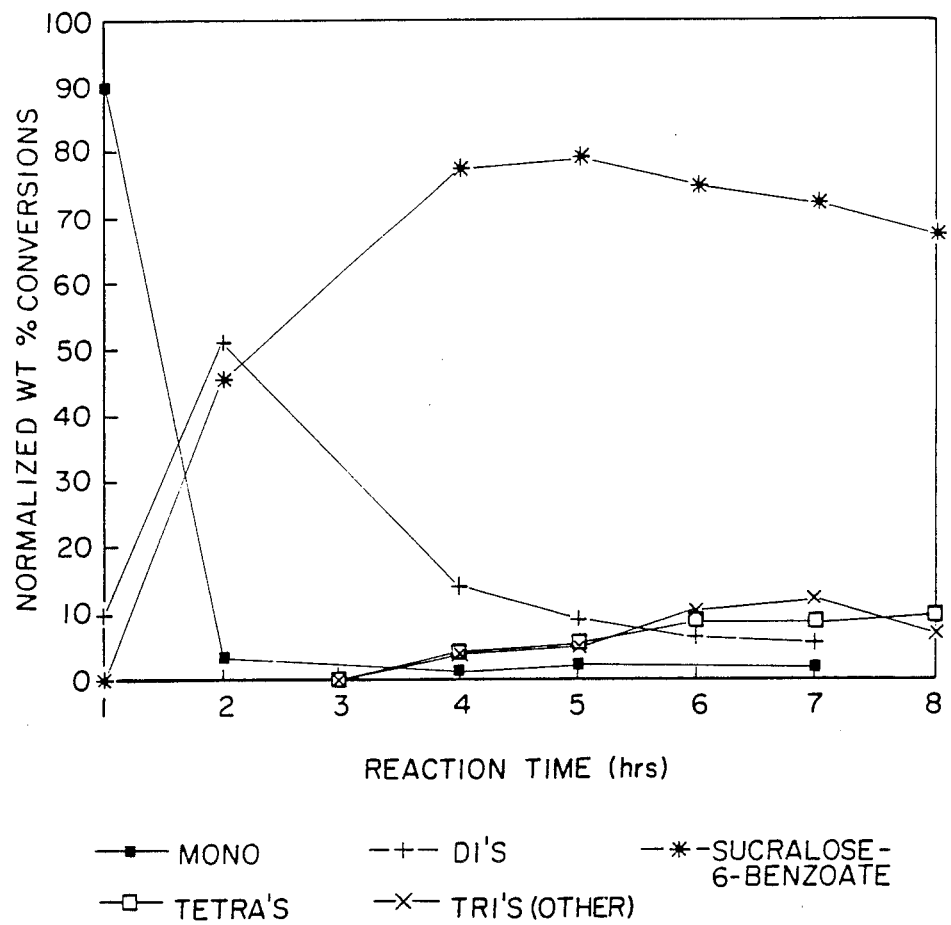

SUCROSE-6-ESTER CHLORINATION

The invention relates to an improved process for the chlorination of sucrose-6-esters to produce selectively chlorinated products.

BACKGROUND OF THE INVENTION

The selective chlorination of less than all the hydroxyl groups of a polyhydric alcohol can be a major synthesis problem, which can be made more complicated if the hydroxyl groups are of differing reactivity. The high intensity sweetener sucralose, a compound whose formal name is 4-chloro-4-deoxy-α-D-galactopyranosyl-1,6dichloro-1,6-dideoxy-β-D-fructofuranoside, is a partially chlorinated derivative of sucrose having chlorine substituted for the hydroxyl groups in the 6', 4, and 1' positions. It is a major synthesis problem to direct the chlorination of sucrose only to the desired 6', 4, and 1' positions to produce sucralose. The initial process disclosed in the literature for the synthesis of sucralose involved the full selective protection of all the hydroxyl groups on the sucrose as follows:

(1) tritylation of sucrose at the 6, 1', and 6' primary hydroxyl groups with trityl chloride in pyridine;
(2) acetylation of the tri-tritylsucrose at the 5 secondary positions;
(3) removal of the trityl groups to give 2,3,4,3', 4'pentaacetylsucrose;
(4) migration of the acetyl group on the 4-position to the 6-position to afford 2,3,6,3', 4'-pentaacetylsucrose;
(5) chlorination of the free hydroxyls to produce sucralose pentaacetate; and
(6) deacetylation of the sucralose pentaacetate.

The above-described process is disclosed, for example, by P. H. Fairclough, L. Hough, and A. C. Richardson, *Carbohydr. Res.*, 40, 285 (1975); L. Hough, S. P. Phadnis, R. Khan, and M. R. Jenner, British Patents Nos. 1,543,167 and 1,543,168 (1979).

Considerable work has been carried out to determine the relative reactivities of the sucrose hydroxyl groups to chlorination. See, for instance, L. Hough, S. P. Phadnis, and E. Tarelli, *Carbohydr. Res.*, 44, 35 (1975). The results indicate that the reactivity is 6 and 6'<4<1'<4-'<others. Thus a mild chlorination yields 6,6'-dichlorosucrose, a more vigorous chlorination gives the 4,6,6'-trichloro species (the 4-position is chlorinated with inversion of configuration, hence the product is 4,6,6'-trichloro-4,6,6'-trideoxyoalactosucrose), and increasingly vigorous chlorinations give successively 4,6,1',6'-tetrachloro-4,6,1', 6'-tetradeoxygalactosucrose and 4,6,1', 4', 6'-pentachloro- 4,6,1', 4', 6'-pentadeoxygalactosucrose. From a consideration of this data it can be seen that blocking the 6-position with a readily removable protecting group such as a benzoate or acetate ester group, followed by trichlorination and removal of the protecting group, could yield sucralose without the need for full protection of all the hydroxyl groups.

The chlorination of partially protected carbohydrates is especially difficult because side reactions, such as oxidation and elimination, have a great tendency to occur. [From reviews dealing with the chlorination of carbohydrates, consult J. E. G. Barnett, *Adv. Carbohydr Chem.*, 22, 177 (1967); and W. A. Szarek, *Adv. Carbohydr. Chem. Biochem.*, 28. 225 (1973).]The relatively severe conditions required to chlorinate the unreactive neopentyl-like 1'- position of sucrose can, and often does, result in a product consisting primarily of dark degradation products and tars. (For reviews which discuss the chlorination of sucrose and its derivatives, consult: R. A. Khan, *Adv. Carbohydr. Chem. Biochem.*, 33, 225 (1976); and M. R. Jenner in "Developments in Food Carbohydrates-2", C. K. Lee, Ed., Applied Science, London, 1980, pp. 91–143.)

Typically, the chlorinated products resulting from the chlorination of sucrose or its derivatives are purified and isolated by chromatographic techniques or by derivitization to form highly crystalline solids (e.g., peracetylation).

BRIEF SUMMARY OF THE INVENTION

The invention provides an improved process for the high-yield preparation of purified sucralose-6-esters, and in particular sucralose-6-benzoate, i. e., 6-O-benzoyl-4-chloro-4deoxy-αD-galactopyranosyl-1,6-dichloro-β-D-fructofuranoside, by the controlled chlorination of sucrose-6-esters. The 1',4,6'-trichloro- sucralose-6-ester product can be purified and isolated in good yields by a combination of extractive and crystallization techniques. The purified, isolated sucralose-6-esters produced by this improved process are suitable for direct conversion to the non-nutritive sweetener sucralose by base-catalyzed ester hydrolysis. The process of the invention comprises the steps of:

(a) adding at least seven molar equivalents of an acid chloride to a reaction mixture comprising a tertiary amide, in the presence of a sucrose-6-ester dissolved in the said reaction mixture, to form initially a chloroformimium chloride salt which subsequently forms an O-alkylformiminium chloride adduct with the hydroxyl groups of the sucrose-6-ester;

(b) subjecting the reaction mixture product of step (a) to an elevated temperature not higher than about 85° C. for a period of time sufficient to produce a mixture of chlorinated sucrose-6-ester products consisting essentially of monochlorosucrose-6-ester (believed to comprise primarily of 4- and 6'-mono-chloro isomers), 4,6'-dichloro-sucrose-6-ester, and 1', 6'-dichloro- sucrose-6-ester; and (c) subjecting the reaction mixture product of step (b) to an elevated temperature not higher than about 125° C. for a period of time sufficient to produce a chlorinated product consisting essentially of 1', 4,6'-trichlorogalacto- sucrose-6-ester.

In a preferred aspect of the process of the invention, the 1',4,6'-trichlorogalactosucrose-6-ester product is recovered by the steps of:

(d) Hydrolysis of the non-chlorinated O-alkylformiminium chloride complexed hydroxyl groups at positions 2,3,3',4' of the trichlorinated sucrose-6-ester with aqueous alkali under such conditions of temperature and pH control as to minimize any concomitant 6-ester saponification. The resulting hydrolysate is preferably stabilized by the addition of sufficient acid to attain an approximately neutral pH; and (e) Extraction of the desired 4,1',6'-trichlorooalacto sucrose-6-ester into an appropriate water-immiscible organic solvent followed by crystallization of the product from an organic solvent, an organic solvent mixture, or preferably from an organic solvent-water mixture, thereby directly obtaining substantially improved yields of high-purity sucralose-6-ester without resorting to chromatographic or derivatization techniques.

THE PRIOR ART

Mufti et al., in U.S. Pat. No. 4,380,476, and Rathbone et al., in U.S. Pat. No. 4,617,269, disclose the chlorination of sucrose-6-esters such as sucrose-6-acetate or benzoate with a chlorinating agent such as a Vilsmeier reagent or sulfuryl chloride to form a trichlorinated sucrose derivative. The relevant teachings of these two patents are epitomized by the experiments described in Rathbone et al., starting at Col. 8, line 40, and in Mufti et al., Col. 9, lines 18–30.

Rathbone, in U. S. Pat. No. 4,324,888, discloses the preparation of mono chlorinated reducing sugars by reacting a reducing sugar with an N,N-dialkyl chloroformiminium chloride.

Walter A. Szarek, "Deoxyhalogeno Sugars", in *Advances in Carbohydrate Chemistry & Biochemistry*, 28,225–307 (1973), at 230–259, discusses the direct replacement of hydroxyl groups by chlorine using various reagents, including chloroformimiminium chloride (pages 250 et seq.).

Viehe et al., in "The Chemistry of Dichloromethyleneammonium Salts ('Phosgenimonium Salts')", *Angew. Chem. Internat. Edit.* 12 (10 ), 808–818 (1973), discusses the reactions of chloromethyleneiminium salts with various compounds, including alcohols (p. 809).

Hanessian et al., "A New Synthesis of Chlorodeoxysugars", Chem. Commun., 1967, 1152–1155, describe the N,N-dimethylchloroformiminium chloride in the synthesis of chlorodeoxy sugars.

Chlorination reagents which have been employed with sucrose and its derivatives include triphenylphosphine and carbon tetrachloride (R. L. Whistler and A. K. M. Anisuzzaman in "Methods in Carbohydrate Chemistry", Vol. VIII, R. L. Whistler and J. N. BeMiller, Eds., Academic Press, New York, 1980, pp. 227–231), various Vilsmeier-type reagents (e.g., a tertiary amide in conjunction with methanesulfonyl chloride or thionyl chloride), and sulfuryl chloride with pyridine. See the Khan and Jenner references cited above, as well as Mufti et al., U. S. Pat. No. 4,380,476. The nucleophilic displacement of methanesulfonate and toluenesulfonate groups has also been employed for the preparation of chlorodeoxysucrose derivatives (see Khan and Jenner).

Eilingsfeld et al., *Angew.Chem.* 72 (22), 836–845 (1960), describe the preparation of N,N-dimethylchloroformiminium chloride from different acid chlorides and carboxylic acid amides.

BRIEF DESCRIPTION OF THE DRAWINGS

FIGS. 4 and 5 are graphs of concentrations of individual components of the reaction mixture of Example 10 versus reaction time;

DETAILED DESCRIPTION OF THE INVENTION

Figure 1:
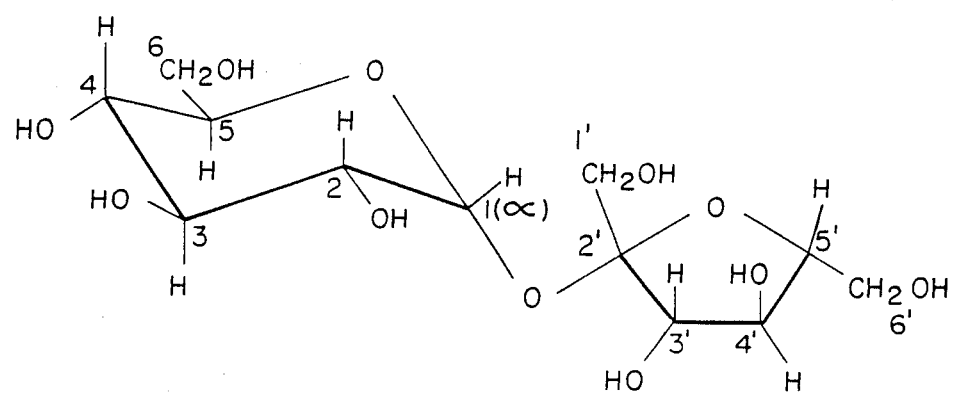
FIG. 1 shows the structural formula for sucrose.
Figure 3:
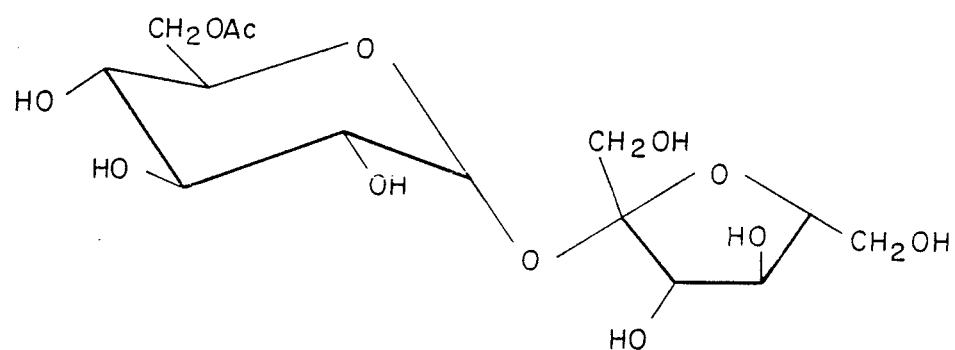
FIG. 3 shows the structural formula for sucrose-6-esters.
Figure 2:
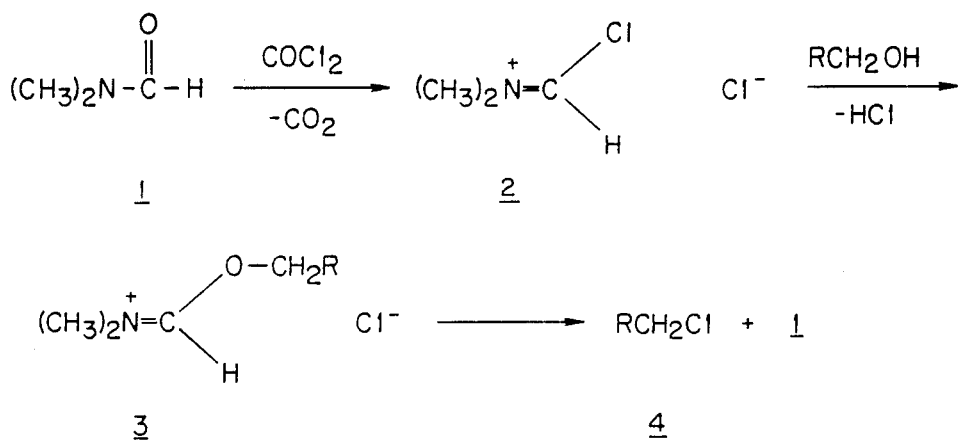
FIG. 2 shows a typical sequence of reactions that occurs in the chlorination process of the invention.

The chlorination reaction that occurs in the process of the invention is illustrated by the reaction sequence shown in FIG. 2 wherein structure 1 is N,N-dimethylformamide (DMF), $COCl_2$ is phosgene, $CO_2$ is carbon dioxide, structure 2 is an illustrative Vilsmeier-type salt or chloroformiminium chloride salt, in this case N,N-dimethylchloroformiminium chloride (a salt known as Arnold's Reagent) that is generated in the presence of substrate sucrose-6-ester by the reaction of an acid chloride (phosgene) with an N-formyl tertiary amide (DMF), $RCH_2OH$ represents the hydroxyl group-containing reaction substrate (in this case, a sucrose-6-ester, which is represented by the structural formula shown in FIG. 3 wherein Ac represents an acyl group such as benzoyl or acetyl), HCl is hydrogen chloride which is present in the reaction mixture as a complex with DMF, structure 3 represents the long-lived intermediate that, along with HCl, is formed by the interaction of the Vilsmeier-type salt 2 with the hydroxyl-group containing reaction substrate, and structure 4 represents the chlorine atom-containing reaction product. To summarize the reactions that occur in the process, as illustrated by the reactants shown in FIG. 2, phosgene first reacts with DMF to form N,N-dimethylchloroformiminium chloride 2 with generation of carbon dioxide; 2 reacts with the hydroxyl-containing compound to form the O-alkylformiminium chloride intermediate shown as 3, with generation of HCl (which forms a complex with DMF). When 3 is heated to an appropriate temperature [which is dependent upon the reactivity of the particular intermediate 3, e.g., relative position reactivities being 6'<4<1'<4'<others (the 6-position being blocked)] a displacement occurs wherein 3 forms the chloride 4 along with regeneration of DMF. This sequence of reactions is known. The major discoveries that are the contributions of this invention are:

(1) that the relative kinetics of the reaction of a chlorinating agent such as phosgene with a tertiary amide such as DMF versus the reaction of the chlorinating agent with sucrose-6-ester so strongly favor reaction with the tertiary amide that it is possible to generate the chloroformiminium chloride reagent in a reaction mixture that also contains the sucrose-6-ester, by addition of phosgene to tertiary amide solutions of sucrose-6-esters under controlled conditions and thereby subsequently generate intermediate 3 directly;

(2) that by increasing the internal temperature of the reaction mixture thus derived, the hydroxyl protected sucrose-6-ester intermediate 3 can be sequentially converted initially into mono- and di-, and trichlorinated sucrose-6-esters. This incremental chlorination approach provides significant improvements in product purity and yield by imparting additional stability to the sucrose-6-ester as sequential chlorine atom substituents are introduced.

(3) that the complexed sucralose-6-ester resulting from (2) above can be liberated by aqueous alkali-mediated hydrolysis under conditions of careful pH and temperature control, and that the resulting crude hydrolysate can be stabilized by adjusting the pH to approximate neutrality;

(4) that the sucralose-6-ester may be extracted from the crude aqueous hydrolysate into an appropriate water-immiscible organic solvent and crystallized from an organic solvent, a mixture of organic solvents, or an organic solvent-water mixture. The organic solvent-water mixture may be either homogeneous or biphasic; the latter case actually constituting an extractive crystallization;

(5) that the solid sucralose-6-ester, particularly sucralose-6-benzoate, isolated as described above can be converted directly to sucralose by alkaline hydrolysis of the ester group.

Since sucrose-6-esters such as sucrose-6-benzoate and sucrose-6-acetate have seven free hydroxyl groups, at least seven molar equivalents of acid chloride are employed in the conversion in order to derivatize each hydroxyl (i.e., to form the intermediate shown as 3 in FIG. 2), even though only the three most reactive hydroxyl groups (positions 4,1′, and 6′) ultimately undergo rearrangement to form the chloride 4. (Upon neutralization of the reaction mixture, the intermediate 3 is decomposed to regenerate the starting hydroxyl group if it had not undergone rearrangement to form 4.)

In addition to sucrose-6-benzoate, other sucrose-6-esters may be used in the invention, including, for example, sucrose-6-alkanoates such as sucrose-6-acetate, and the like. The purpose of the 6-ester group is simply to shield the hydroxyl on the 6 position on the sucrose molecule from the chlorination reaction; accordingly, any ester group that is stable to the conditions of the chlorination reaction and which can be removed by hydrolysis under conditions that do not affect the remainder of the trichlorinated sucrose can be employed.

Several other acid chlorides, besides phosgene, known to form chloroformiminium chloride salts when reacted with tertiary amides, may be used as chlorine sources in the process of the instant invention. These acid chlorides include phosphorous oxychloride, phosphorous pentachloride, thionyl chloride, oxalyl chloride, methanesulfonyl chloride, and the like.

The use of a tertiary amide as both reaction solvent and as substrate for chloroformiminium chloride salt formation is a preferred method for the practice of the invention. Inert diluents, however, such as toluene, o-xylene, 1,1,2-trichloroethane, 1,2-diethoxyethane, diglyme (diethylene glycol dimethyl ether), and the like, can be employed at up to about 80 vol % or more of the liquid phase of the reaction medium, in addition to the tertiary amide. Useful cosolvents are those which are both chemically inert and which provide sufficient solvent power to enable the reaction to become essentially homogeneous at the monochlorination stage. Cosolvents with boiling points substantially below the reaction temperature required by the trichlorination stage can be employed in pressurized systems.

DMF is the preferred tertiary amide for the practice of the invention from the viewpoints of chemical functionality and economic factors. Other tertiary amides which possess N-formyl groups, such as N-formylpiperidine, N-formylmorpholine, N,N-diethylformamide, and the like, can be employed in the process.

A generalized description of a preferred mode for carrying out the process of the invention is set forth below, using phosgene as the acid chloride, DMF as the N-formyl tertiary amide, and sucrose-6-benzoate as the illustrative sucrose-6-ester:

Sucrose-6-benzoate is dissolved in two and one-half to five volumes of DMF and cooled to about 0° C or lower. (Note that in this description "volumes of solvent" is defined as liters of solvent per one kilogram of sucrose-6-benzoate, and all temperatures given are internal reaction temperatures.) A 50 to 75 wt % solution of phosgene (7.5-11 molar equivalents relative to sucrose-6-benzoate) in toluene is then rapidly added with efficient agitation. Alternatively, pure phosgene may be added directly without toluene. The phosgene addition is strongly exothermic (due to the formation of N,N-dimethylchloroformiminium chloride and the reaction of this salt with sucrose-6-benzoate hydroxyl groups to form the intermediate shown as 3 in FIG. 2) and continued cooling is required since attaining temperatures greater than about 60°-70° C. during the addition can adversely affect the course of the reaction. Easily stirred solids are formed in the reaction medium during the phosgene addition. This situation (i.e., wherein the chloroformiminium chloride salt is formed in the presence of sucrose-6-ester dissolved in the same reaction mixture) contrasts with the situation that arises when the chloroformiminium chloride salt, derived from phosgene and DMF, is prepared in the absence of sucrose-6-ester, in which latter situation copious amounts of solids are formed which gives rise to mixing and heat transfer difficulties.

The reaction temperature is then raised over a suitable period of time to a threshold temperature sufficient to effect substantial monochlorination of the sucrose-6-ester, as evidenced by the complete dissolution of all solids in the reaction flask. Temperatures at which this occurs are found within the range of 50° C. to about 70° C., but typically from about 60° C. to 65° C. The reaction medium becomes homogeneous at this point and monochlorinated sucrose-6-benzoate derivatives are seen upon silica-gel TLC analysis (4.00:0.85:0.15, $CHC_3$—$CH_3OH$—HOAC) of a worked-up reaction aliquot. The reaction mixture may be maintained at this temperature for at least 1 hour with little or no di- or higher chlorination occurring. Preferably, the internal temperature is raised further immediately upon attaining a homogeneous reaction medium.

The reaction mixture is rapidly heated to a temperature sufficient to complete monochlorination and effect partial dichlorination of the sucrose-6-ester. Temperatures for this step are usually found within the range of 75° C. to 100° C. and preferably from about 80° C. to 85° C. At this temperature little or no tri- or higher chlorination occurs and a mixture of primarily monochlorinated sucrose-6-esters plus some dichlorinated sucrose-6-esters results after about 1 hour. Mono and dichlorinated sucrose-6-benzoate derivatives are seen by silica-gel TLC to be formed during this period (same solvent system as previously described). Maintenance of the reaction mixture at this temperature for longer periods of time results in a higher degree of conversion of monochlorinated sucrose-6-esters to dichlorinated sucrose-6-esters with little or no trichlorination observed by silica gel TLC. In preferred aspects of the invention, the temperature is increased rapidly, after initially attaining 80°-85° C., to a temperature sufficient to completely convert monochlorinated sucrose-6-esters to dichlorinated sucrose-6-esters, trichlorinated sucrose-6-esters and little or no tetra- or higher chlorinated sucrose-6-esters. Temperatures for this step are usually in the range of about 100° C. to about 130° C. and preferably from about 110° C. to about 125° C. The reaction mixture is held at this temperature for a period of time sufficient to maximize trichlorination, e.g., from about 1 to about 6 hours, and preferably from about 2 to about 4 hours. During this time sucralose-6-benzoate is seen to form by silica gel TLC (same system as previously described).

The temperature increase regimen for the above described reactions is typically conducted over a period of time ranging from about 5 minutes to about 5 hours prior to stabilizing at about 110° C. to 125° C. The use of longer temperature increase times is in no way detrimental to the course of the reaction, but offers no inherent advantage. Preferably, the temperature gradient is conducted over a 20-30 min. period, which is sufficient to convert all of the sucrose-6-ester to a mixture of mono- and dichlorinated sucrose-6-esters prior to submission to the harsher trichlorination temperature conditions. Alternatively, discrete incremental heating steps may be employed to effect sequential chlorination stages, however no particular advantages are attendant thereto over a steeper temperature gradient.

The reaction mixture is then cooled to from about 0° C. to about 40° C. and rapidly treated with about one to 1.5 molar equivalents (relative to the acid chloride, phosgene in this illustrative procedure) of cold aqueous alkali metal hydroxide, such as sodium or potassium hydroxide, or an aqueous slurry of an alkaline earth metal oxide or hydroxide, such as calcium oxide or calcium hydroxide. This neutralization is strongly exothermic. As excessively high temperatures will cause side reactions (e.g., anhydro derivative formation, debenzoylation, etc.) resulting in a loss of sucralose-6-benzoate, temperatures are held below about 80° C. during this operation. For optimum yield, the final pH of the reaction mixture is preferably within the range of about 8.5 to about 11, and preferably from about 9 to about 10. Careful control of the pH is required to minimize the potential of concurrent sucralose-6-ester deacylation.

The crude chlorination reaction product may also be quenched by adding the warm (70°-110° C.) DMF solution to about one to 1.5 molar equivalents (relative to acid chloride) of cold aqueous alkali such as sodium or potassium hydroxide, or a cold aqueous slurry of an alkaline-earth metal oxide or hydroxide, such as calcium oxide or calcium hydroxide, with vigorous agitation. As in the above-described neutralization method, control of pH and temperature is preferred in order to avoid diminished yields resulting from anhydrosugar formation, debenzoylation etc.

The chlorination reaction can also be quenched with concentrated aqueous or alcoholic ammonia using either mode of addition. This process, however, is less preferred because of the economic disadvantages inherent in the disposal of ammonia-containing wastes.

Following alkali treatment, the crude aqueous product mixture is neutralized to about pH 6-8 with, for example, acetic acid or dilute mineral acid, then intimately contacted with an organic solvent capable of extracting sucralose-6-benzoate from the mixture, but which has less affinity for the extraction of the underchlorinated carbohydrate derivatives in the aqueous phase. Water-immiscible organic solvents suitable for this purpose include ethers, such as methyl tert-butyl ether (MTBE); esters, such as ethyl acetate; ketones, such as 2-butanone; chlorinated hydrocarbons, such as methylene chloride; mixtures of the above with hydrocarbons such as toluene, and the like, with ethyl acetate being a preferred solvent because of extraction efficiency, and MTBE being a preferred solvent because of selectivity and economic considerations. The extraction operation is normally conducted several times, typically between 2 and 6 times and preferably between 3 and 4 times, and the organic extracts combined and washed with water to remove DMF and small amounts of underchlorinated sucrose-6-benzoate contaminants. Alternatively, the extraction may be conducted in a continuous manner using standard commercially available continuous extraction equipment.

The combined organic extracts can at this point be treated with activated carbon to remove resinous contaminants, and then filtered. For extracts wherein the product, sucralose-6-ester, has limited solubility, the filtrate may be evaporated under reduced pressures at from about 30° C. to about 80° C. to a concentration suitable for direct crystallization. In the case of certain extracts, particularly MTBE extracts, of the product, it is advantageous to reduce the volume as described above and then add water to attain a water/MTBE ratio of from about 4:1 to about 1:2, and preferably from about 3:1 to 1:1, in conjunction with vigorous agitation of the resulting biphasic mixture. Solid sucralose-6-ester, and particularly sucralose-6-benzoate, rapidly crystallizes from such a mixture which constitutes, in effect, an extractive crystallization since impurities are preferentially extracted into either the aqueous or organic solvent phases. Total solvent volumes (i.e., MTBE and water combined) of from about two and one-half to about 10 volumes relative to the theoretical amount of sucralose-6-ester present are useful for this stage of the process, with from about five to seven and one-half volumes being preferred.

Alternatively, for extracts wherein the product sucralose-6-benzoate is highly soluble (e.g. halogenated hydrocarbons, esters, ketones), the extracts are evaporated under reduced pressures at from about 30° C. to about 80° C. to afford a crude sucralose-6-ester syrup which is directly treated with an appropriate organic solvent, organic solvent mixture, or organic solvent/water mixture in the above described proportions to affect crystallization. Suitable crystallization solvents include alcohols, hydrocarbons, ethers, esters, ketones and combinations of the above with each other or with water.

Finally, sucralose-6-benzoate may be crystallized directly from extraction solvents in which they have appreciable solubility (e.g. halogenated hydrocarbons, and the like) after concentration of the extracts to a volume wherein the solubility saturation level of the product is exceeded. This typically results in lower recoveries of the sucralose-6-ester and is hence not preferred.

Following sucralose-6-benzoate crystallization, the product slurry is typically allowed to cool to room temperature with vigorous agitation, and the solid product filtered, washed with a small amount of an appropriate solvent such as MTBE, and vacuum dried with mild heating. Molar yields of solid sucralose-6-benzoate, based on sucrose-6-benzoate and corrected for purity, of from about 45 to about 60% are routinely obtained using the processing methods described above. The dried product typically contains 85-90% sucralose-6-benzoate, 2-15% of two dichlorinated sucrose-6-benzoate derivatives, and 2-3% of a tetrachlorinated derivative (HPLC analysis). An additional 3-6% molar yield of sucralose-6-benzoate is typically contained in the mother liquors.

The resulting purified sucralose-6-esters, and in particular sucralose-6-benzoate, are directly suitable for conversion into the commercially valuable, nonnutritive sweetener sucralose. Optionally the solid sucralose-6-ester may be further purified by recrystallization from an appropriate solvent or solvent mixture (e.g.: methanol or methanol and water). The process for the conversion of sucralose-6-benzoate to sucralose is comprised of the following steps:

(a) Alkaline hydrolysis in a lower alkanol solvent, preferably methanol, by a catalytic amount of an alkali metal hydroxide, preferably potassium hydroxide, at from about 25° C. to about 40° C. for a sufficient period of time from about 5 minutes to about 60 minutes.

(b) Neutralization of the reaction mixture from (a) by the addition of either an appropriate amount of a protic acid, or by treatment of the reaction mixture of step (a) with the protic acid form of an ion exchange resin.

(c) Removal of the lower alkanol solvent employed in the above steps by evaporation, and then dissolving the crude product in water.

(d) Purification of the crude sucralose from contaminants present in the aqueous solution of (c) above (e.g.: alkyl benzoate etc.) by extraction with an appropriate water-immiscible organic solvent in which the contaminants are soluble, but in which the sucralose is not. Alternatively, the alkyl benzoate may be removed by azeotropic codistillation with a portion of the water employed to produce the solution in step (c).

(e) Optionally, the aqueous solution of purified sucralose resulting from step (d) may be treated with activated carbon to remove colored impurities at from about 25° C. to about 50° C. over from about 15 minutes to about 60 minutes.

(f) Recovery of the purified sucralose of step (d) or optionally of step (e) above by partial evaporation of the water, cooling and filtration of the crystalline product thus obtained. The mother liquor is suitable for recycle into another crystallization wherefrom additional product is obtained.

EXAMPLE 1

100-Gram Scale Chlorination of Sucrose-6-Benzoate with Phosgene

A 3000-ml, four-neck, round-bottom flask, equipped with mechanical stirrer, thermometer, addition funnel, and reflux condenser topped with an argon inlet, was charged with 102 g of 98.1% sucrose-6-benzoate (100 g, 0.224 mol) and 500 ml of DMF. The mixture was stirred under argon until homogeneous, and then cooled to $-33°$ C. in a dry ice-acetonitrile bath. This solution was rapidly treated in three portions with a total of 244 g (2.46 mol) of phosgene in about 65 ml of toluene. During the phosgene addition, the temperature of the reaction mixture increased from $-33°$ C. to $+16°$ C. with the cooling bath kept in place.

The reaction mixture, which contained light suspended solids, was heated over a period of 20 min to 65° C. at which point the mixture was clear and golden yellow in color. The solution was heated to 85° C. over 25 min and the resulting burgundy colored solution held at this temperature for 60 min. The mixture was then heated over 20 min to 115° C. and held at this temperature for 4.5 hr.

The reaction mixture was then cooled to 10° C., and treated in one portion with 620 ml of ice-cold 4N NaOH (2.48 mol) with vigorous stirring. The temperature of the reaction mixture was 50° C. after the addition was complete, and the final pH was about 9. The reaction mixture was vigorously stirred for about 3 min, and then neutralized to about pH 7 by the addition of about 4 ml of glacial acetic acid.

The crude product mixture was treated with 750 ml of ethyl acetate and stirred gently for about 5 min. The layers were separated and aqueous layer further extracted with ethyl acetate (6×600 ml). The organic extracts were combined, washed with water (1 ×1000 ml), and then treated with about 20 g of activated carbon for about 5 min at 50° C. This slurry was filtered through Celite and the cake washed with an additional small amount of ethyl acetate.

The resulting clear yellow filtrate was evaporated to a syrup at 50° C. under water aspirator vacuum. The syrup was treated with 500 ml of $H_2O$ and 250 ml of MTBE with thorough mixing at 50° C. The biphasic mixture dissolved the syrup and after about 5 min rapidly deposited crystalline sucralose-6-benzoate. The product was filtered, washed with MTBE (2×150 ml), and vacuum dried (50° C./16hr/0.5 mm of Hg) to afford 76.3 g of colorless solid. HPLC analysis showed this product to contain 86.8 wt % sucralose-6-benzoate (66.3 g, 0.132 mol, 58.9% yield).

Sucralose-6-benzoate samples were analyzed by high-pressure liquid chromatography (HPLC). Sample components were separated on a reverse-phase octadecylsilane column employing a linear 50-minute gradient from 24% methanol-76% pH 7.5 0.01M $K_2HPO_4$ buffer to 69.5% methanol-30.5% buffer. Detection was by ultraviolet absorption at 254 nm. Samples were analyzed in comparison to a sucralose-6-benzoate standard of highest available purity to estimate weight percent composition. Chromatographic purity was also calculated from the total chromatographic peak profile.

EXAMPLE 2

Reproducibility of the Chlorination of Sucrose-6-Benzoate with Phosgene

The experimental procedure described above was employed to convert three additional 100-gram batches of sucrose-6-benzoate into sucralose-6-benzoate. The four preparations provided a total (corrected for purity) of 261.6 g of crystalline sucralose-6-benzoate with an average yield of 58.2% of theoretical. The relevant data have been compiled into the table below. The third experiment in the table corresponds to Example 1. The fourth example in the table refers to an experiment performed precisely as in Example 1, except that the phosgene was added as a neat liquid to the sucorse-6-benzoate/DMF reaction solution, no toluene diluent being employed.

| (1) EXP | (2) RXN TIME | (3) WT DRIED SOLID | (4) % PURITY BY HPLC | (5) WEIGHT PRODCT | % YIELD | (6) DICHLORO DERIVS | (6) TETRACHLORO DERIVS |
|---|---|---|---|---|---|---|---|
| 1 | 375 | 81.1 | 78.4 | 63.6 | 56.6 | 10.1 | 1.9 |
| 2 | 378 | 74.9 | 87.3 | 65.4 | 58.2 | 11.8 | 2.1 |

-continued

| (1) EXP | (2) RXN TIME | (3) WT DRIED SOLID | (4) % PURITY BY HPLC | (5) WEIGHT PRODCT | % YIELD | (6) DICHLORO DERIVS | (6) TETRA-CHLORO DERIVS |
|---|---|---|---|---|---|---|---|
| 3 | 390 | 76.3 | 86.8 | 66.3 | 58.9 | 16.5 | 2.6 |
| 4 | 405 | 78.5 | 84.5 | 66.3 | 58.9 | 8.2 | 2.8 |

(1) All four experiments were conducted with 100 g (corrected for purity) sucrose-6-benzoate, 500 ml of DMF, and 11.0 mol equiv of phosgene essentially as described in the preceding Example.
(2) Reaction times in min include heating periods between desired reaction temperatures.
(3) Weight of dried solid product in grams.
(4) Wt % sucralose-6-benzoate content of dried solid by HPLC analysis.
(5) Weight of sucralose-6-benzoate in grams.
(6) Wt % of dichloro- and tetrachlorosucrose-6-benzoate contaminants in the isolated product with structural assignments predicted from HPLC behavior only. Note that the totals exceed 100% in the latter two cases. The assay method for sucralose-6-benzoate has an accuracy of ±2% of the value indicated, and the situation is less certain for the other chlorinated derivatives since reliable reference standards are not available.

(1) All four experiments were conducted with 100 g (corrected for purity) sucrose-6-benzoate, 500 ml of DMF, and 11.0 mol equiv of phosgene essentially as described in the preceding Example.

(2) Reaction times in min include heating periods between desired reaction temperatures.

(3) Weight of dried solid product in grams.

(4) Wt % sucralose-6-benzoate content of dried solid by HPLC analysis.

(5) Weight of sucralose-6-benzoate in grams.

(6) Wt % of dichloro- and tetrachlorosucrose-6-benzoate contaminants in the isolated product with structural assignments predicted from HPLC behavior only. Note that the totals exceed 100% in the latter two cases. The assay method for sucralose-6-benzoate has an accuracy of ±2% of the value indicated, and the situation is less certain for the other chlorinated derivatives since reliable reference standards are not available.

EXAMPLE 3

Mass Balance for the Chlorination of Sucrose-6-Benzoate with Phosgene

HPLC analysis of the stripped mother liquors obtained from the initial crystallization of sucralose-6-benzoate in experiment 1 of Example 2 indicated that the MBBE-based crystallization is very efficient. Only 5.8% of the total extracted quantity of sucralose-6-benzoate remained in the mother liquors. Analysis of the crystalline solid and the mother liquors, assuming no significant differences in the molar absorptivities of the various chlorinated derivatives, accounted for 85.6% of the total mass balance. This treatment does not account for materials which may have lost the benzoate chromophore (e.g., sucralose from over hydrolysis), or extremely water-soluble intermediates which would certainly have been lost into the initial quench solution (e.g., monochloro- and dichlorosucrose-6-benzoate derivatives from under chlorination).

| (1) Component | Grams (main crop) | Grams (mother liquors) | Total Grams | mmoles |
|---|---|---|---|---|
| Monochloro (MW = 464.86) | — | 2.20 | 2.20 | 4.74 |
| sucralose-6-benzoate (MW = 501.74) | 63.60 | 4.14 | 67.74 | 135.0 |
| Other Trichloros (MW = 501.74) | — | 0.56 | 0.56 | 1.1 |
| Dichloros (MW = 483.29) | 8.20 | 13.69 | 21.89 | 45.3 |
| Tetrachloros (MW = 520.19) | 1.54 | 1.49 | 3.03 | 5.8 |
| TOTAL | | | | 191.9 |
| Substrate Charged (corrected for purity) | | | | 224.1 |
| Mass Balance Accounted for = 85.63% | | | | |

(1) With the exception of sucralose-6-benzoate, structural assignments have been predicted from HPLC behavior.

EXAMPLE 4

Proton and Carbon NMR Spectral Assignments for Sucralose-6-Benzoate

A sample of sucralose-6-benzoate was recrystallized from MTBE. This purified sample (93.6 wt % sucralose-6-benzoate by HPLC, mp 106–7° C.) was subjected to $^1$H and $^{13}$C NMR spectroscopy. Structural assignments for the proton spectrum were made with the assistance of supplemental $D_2O$ shift and proton decoupling data. The carbon spectral assignments were derived from appropriate polarization and 2-d experiments.

| $^1$H-NMR ASSIGNMENTS (Aliphatic Resonances) SUCRALOSE-6-BENZOATE (ACETONE-$d_6$) | | | | |
|---|---|---|---|---|
| δ ppm | J (Hz) | | Mult | Assign |
| 5.492 | 1,2 | 3.8 | d | H1 gal |
| 4.862 | — | | m | H5 gal |
| 4.603 | 4,5 | 1.35 | dd | H4 gal |
|  | 3,4 | 3.7 | | |
| 4.516 | 5,6a | 6.9 | dd | H6a gal |
|  | 6a,6b | 11.4 | | |
| 4.406 | 5,6b | 5.1 | dd | H6b gal |
| 4.283 | 3',4' | 8.1 | d | H3' fruct |
| 4.241 | 3,4 | 3.6 | dd | H3 gal |
|  | 2,3 | 10.0 | | |
| 4.104 | 4',5' | 7.8 | t | H4' fruct |
| 3.924 | — | | dd | H2 gal |
| 3.901 | 5',6'b | 2.1 | dt | H5' fruct |
|  | 4',5' | 7.8 | | |
|  | 5',6'a | 10.7 | | |
| 3.82 | — | | m | H6' fruct |
| 3.82 fruct | — | | m | H1'a,b |
| 3.603 | 6'a,6'b | 11.4 | dd | H6'b fruct |

| $^{13}$C NMR CORRELATIONS FOR SUCRALOSE-6-BENZOATE (Carbohydrate Resonances) | |
|---|---|
| Assignment | Obs Shift (acetone) δ (ppm) |
| C2' | 104.6 |
| C1 | 93.6 |
| C5' | 83.4 |
| C3' | 77.9 |

| | |
|---|---|
| C4' | 77.3 |
| C5,C3,C2 | 69.0 |
| C6 | 65.5 |
| C4 | 65.0 |
| C6' | 46.3 |
| C1' | 44.6 |

NOTES:
1. Sample run in acetone - d-6/500 MH$_2$
2. Assignments verified by decoupling and 2-d experiments
3. s = singlet
   d = doublet
   dd = doublet of doublets
   t = triplet
   m = multiplet

EXAMPLE 5

100 -Gram Scale Chlorination of Sucrose -6-Benzoate with Phosphorus Oxychloride

A 2000- ml, four-neck, round-bottom flask, equippd with mechanical stirrer, thermometer, addition funnel, and reflux condenser topped with an argon inlet, was charged with 400 ml of DMF and cooled to −5° C. Phosphorus oxychloride (253 g, 154 ml, 1.65 mol) was added dropwise over 20 min with stirring and continued cooling under argon, and then a solution of 110 g of 91.2% sucrose-6-benzoate (100 g, 0.224 mol) in 193 ml of DMF was added dropwise over 21 min with stirring and continued cooling under argon. The reaction temperature was not allowed to exceed +8° C. during the course of the two additions.

The homogeneous pale-yellow reaction mixture was heated over 25 min to 60° C. and held at this temperature with stirring under argon for 5 min. The solution was heated to 83° C. over 15 min and held at this temperature for 65 min. The reaction temperature was then increased to 115° C. over about 20 min and held at this temperature for 187 min. During this latter period the reaction mixture darkened to a deep burgundy and thickened slightly.

The reaction mixture was allowed to cool to about 100° C., and then poured in one portion with vigorous stirring into 1300 ml of 4N KOH (5.20 mol) containing about 200 g of ice. The dark reaction mixture was placed in a separatory funnel and extracted with toluene (1×1000 ml), and the toluene extract washed with 460 ml H$_2$O. The toluene solution was discarded, and the combined aqueous phases were extracted with ethyl acetate (5×500 ml). The combined organic extracts were washed with water, brine, dried over MgSO$_4$, evaporated under reduced pressure, and then dried under high vacuum to give 67.7 g of a pale-brown frothy solid shown by HPLC to contain 52.9 wt % sucralose-6-benzoate (35.8 g, 71.4 mmol, 31.9% yield).

The crude product was treated for 15 min at 50°-60° C. with 150 ml of H$_2$O and 100 ml of MTBE with vigorous stirring. The mixture was allowed to cool slightly and the crystalline solid thus produced filtered, washed with toluene (2×50 ml), and vacuum dried (25° C./18 hr/0.1 mm of Hg) to give 44.4 g of off-white solid shown by HPLC to contain 67.7 wt % sucralose-6-benzoate.

EXAMPLE 6

Chlorination of Sucrose-6-Benzoate with Phosphorus Pentachloride

A 100-ml, three-neck, round-bottom flask, equipped with thermometer, argon inlet, and magnetic stir bar, was charged with 43 ml of DMF. With magnetic stirring under argon, the DMF was treated portionwise with 15.4 g (74.0 mmol) of phosphorus pentachloride. The warm slurry of Vilsmeier-type reagent thus produced was cooled to about 0° C., filtered, and the solids thus obtained washed with DMF (1 ×25 ml) and diethyl ether (2×50 ml).

The nearly colorless solid was placed in a 100-ml, three-neck, round-bottom flask, equipped with argon inlet, reflux condenser, addition funnel, and magnetic stir bar, along with 40 ml of DMF. With magnetic stirring under argon at 0°-5° C., this slurry was treated dropwise over about 5 min with 3.00 g of 90.8% sucrose-6-benzoate (2.72 g, 6.11 mmol) in 20 ml of DMF. After stirring for 5 min at 5° C., the mixture was stirred for 60 min at ambient temperature to give a clear gold-colored solution.

The reaction mixture was stirred under argon and sequentially heated at 60° C. for 1.5 hr, 80° C. for 16 hr, and 100° C. for 8 hr. The reaction was then allowed to cool to room temperature, and with rapid stirring poured into 150 ml of concentrated aqueous NH$_4$OH—CH$_3$OH (1:1). The methanolic solution was diluted with 350 ml of H$_2$O and extracted with ethyl acetate (5×100 ml). The combined organic extracts were washed with water, brine, and dried over NgSO$_4$. Evaporation of the solvent followed by drying under high vacuum afforded 3.30 g of a reddish brown gum shown by HPLC to contain 44.6 wt % sucralose-6-benzoate (1.47 g, 2.93 mmol, 48.1% yield).

EXAMPLE 7

Chlorination of Sucrose-6-Benzoate with Phosgene Iminium Chloride

A 100-ml, three-neck, round-bottom flask, equipped with thermometer, addition funnel, reflux condenser topped with an argon inlet, and magnetic stir bar, was charged with 30 ml of DMF and 7.27 g (44.8 mmol) of phosgene iminium chloride (Cl$_2$C=N$^+$ME$_2$Cl$^-$, Aldrich Chemical Company. catalog #16,287-6). This slurry was treated dropwise with cooling to about 20° C. with 2.00 g of 90.8% sucrose-6-benzoate (1.82 g, 4.07 mmol) in 20 ml of DMF. This slurry was stirred at ambient temperature for 15 min, and then stirred under argon and sequentially heated at 60° C. for 1 hr (mixture homogeneous at this point), 85° C. for 14 hr, and 100° C. for 24 hr.

The reaction was allowed to cool to room temperature and poured into a mixture of 50 ml concentrated aqueous NH$_4$OH-50 ml H$_2$O-25 g ice with vigorous stirring. The dark aqueous mixture was saturated with NaCl, transferred to a separatory funnel, and extracted with ethyl acetate (1×100 ml followed by 3×50 ml). The combined organic extracts were washed with water, brine, and dried over MgSO$_4$. Evaporation of the solvent followed by drying under high vacuum gave 2.60 g of a reddish-brown gum shown by HPLC to contain 47.1 wt % sucralose-6-benzoate (1.22 g, 2.44 mmol, 60.0% yield).

EXAMPLE 8

Recovery of Sucralose -6-Benzoate by Continuous Extraction with Tert -Butyl Mmthyl Ether A 1000-ml, 4-neck, round-bottom flask, equipped with overhead stirrer, 250-ml pressure-equalizing addition funnel, thermometer and simple distillation apparatus, was purged with argon and charged with sucrose-6- benzoate [85.5 g (93.6%); 0.18 mol] and 480 ml DMF. The system was evacuated (mechanical pump) and 75 ml of distillate collected at 40°–45° C.

The system was vented to atmospheric pressure with argon, the distillation apparatus replaced with a dry ice cold-finger condenser and $COCl_2$ (122 ml, 1.7 mol) added to the pressure-equalizing addition funnel. The solution in the reaction flask was cooled to $-10°$ C. and $COCl_2$ was added to the cold reaction mixture over 15 min while keeping the temperature of the mixture between $-5$ to $+10°$ C.

When the addition was completed, the cooling bath was removed and the temperature of the mixture rose to 20° C. The mixture was heated further (oil bath) to 60° C. over 10 min, then to 100° C. over 25 min, kept at 113°–115° C. for 3.5 hr, cooled to 10° C. and quenched by rapid addition of 450 ml 4M NaOH at 0° C. The resulting exotherm brought the temperature to 45°–50° C. The alkaline (pH 10) solution was neutralized by addition of 7 ml glacial acetic acid.

The reaction mixture was kept at 40°–45° C. with an oil bath, the cold-finger condenser replaced with equipment for continuous extraction with a solvent less dense than water and the mixture extracted 24 hrs with 750 ml MTBE at 40°–45° C.

The organic phase was found to contain 58.7 g sucralose-6-benzoate (65.3% molar yield), with lesser amounts of other chlorination by-products. Addition of water (0.2 L) to the extract, with concurrent agitation, resulted in crystallization of the sucralose-6-benzoate which was recovered by filtration and vacuum dried (50° C./18hr/0.5 mm Hg) to afford 53.6 g of colorless solid. HPLC analysis showed this product to contain 94.0% wt % sucralose-6-benzoate (50.4 g, 0.100 mol, 55.8% yield).

DEBENZOYLATION OF MTBE-CRYSTALLIZED SUCRALOSE-6-BENZOATE

A portion of the sucralose-6-benzoate crystallized above (20 g) was debenzoylated with 0.15%-wt KOH in methanol (4 hrs at ambient temperature). The reaction mixture was neutralized with Amberlyst IRC 50 (H+), the neutral mixture was filtered to remove the resin, and the resin was washed with 2×35 ml methanol and 2×50 ml warm water (70° C.).

The combined filtrate and washes were evaporated to a thick syrup which was diluted with water (100 ml), then extracted with 2×30 ml ethyl acetate to remove non-polar impurities. The ethyl acetate extract was concentrated to half volume and back extracted with water. Combined aqueous solution and backwash were concentrated to give 112.5 g of an aqueous solution which contained 13.5 g (91% yield) of sucralose which was 97.9% pure. A portion of this material was carried on to crystalline product (56.4% recovery) which was 99.5% pure.

EXAMPLE 9

Chlorination of Sucrose-6-Benzoate with Phosgene using A Co-Solvent

A 500-ml, three-neck, round-bottom flask, equipped with oil bath, magnetic stir bar, addition funnel, reflux condenser, and argon inlet, was charged with 20 g of 91.2% sucrose-6-benzoate (18.2 g, 40.9 mmol) and 60 ml of DMF. The mixture was stirred at room temperature under argon until homogeneous, and then cooled to about $-10°$ C. and treated in one portion with 32.3 g (327 mmol) of phosgene in 40 ml of 1,2-diethoxyethane. During the phosgene-diethoxyethane addition, the temperature increased to about $+15°$ C. with the cooling bath kept in place.

The extremely viscous reaction mixture was stirred under argon and sequentially heated to 65° C. over 20 min and held at this temperature for 45 min, 85° C. over 25 min and held at this temperature for 45 min, and 115° C. over 35 min and held at this temperature for 86 min. The reaction mixture became mobile and biphasic during the course of the reaction.

The reaction mixture was cooled and treated with 164 ml of ice-cold 2N NaOH (328 mmol). The crude aqueous mixture was treated with 200 ml of ethyl acetate, stirred gently for 5 min, and the mixture transferred to a separatory funnel and the layers separated. The aqueous layer was further extracted with ethyl acetate, and the organic extracts combined and washed with water. The organic solution was then boiled briefly with decolorizing carbon and filtered through Celite.

The ethyl acetate solution was evaporated and the crude product processed in the usual manner with $H_2O$-MTBE to afford 16.2 g of colorless solid shown by HPLC to contain 46.0 wt % sucralose-6-benzoate (7.45 g, 14.9 mmol, 36.3% yield).

EXAMPLE 10

Figure 5:
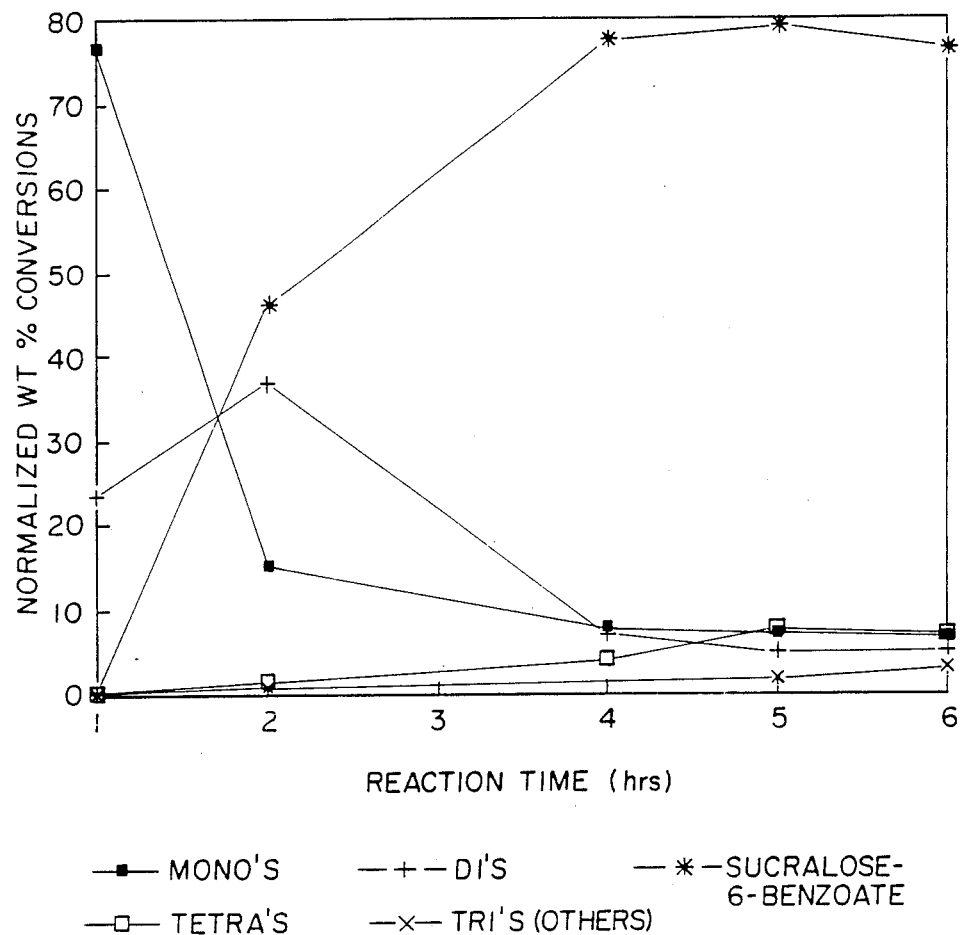

Reaction Profile of the Chlorination of Sucrose -6-Benzoate with Phosphorus Oxychloride The phosphorus oxychloride-based chlorination of sucrose-6-benzoate was conducted with and without LiCl and molecular sieves added to the reaction. The molecular sieves were added to absorb any tar that might form during the chlorination reaction. It has not been found that there is any advantage in using molecular sieves; therefore, their use is not preferred. The lithium chloride was added because it was felt that it might accelerate the chlorination, especially the introduction of the third chlorine atom on the sucrose molecule. It did not seem to have any beneficial effect, and therefore its use is not preferred. Aliquots were withdrawn periodically over the course of the reactions, neutralized with ammonia, and worked up extractively with ethyl acetate. The aliquots were analyzed by HPLC to obtain wt % values for all chlorinated species with the molar absorbtivities of the various chlorinated products assumed to be identical to that of sucralose-6-benzoate. The wt % assays for the individual components were plotted versus reaction time in order to obtain the reaction profiles illustrated in FIGS. 4 and 5, respectively.

Both plots are qualitatively the same with sucralose-6-benzoate generation maximizing after 1 hour at 80-5° C. followed by 3.5 hours at 115° C. The reaction which employed sieves and lithium chloride (plot shown in FIG. 4) exhibited a faster conversion of mono- to dichlorosucrose-6-benzoate derivatives (maximum after 1 hour at 80-5° C.) whereas the reaction not employing additives (plot shown in FIG. 5) maximized in dichlorosucrose-6-benzoate derivatives after 1 hour at 80-5° C. and 1 hour at 115° C. Both plots indicate that sucralose-6-benzoate content drops off markedly after 4 hours at 115° C. The dichloro isomers decrease asymptotically and are present to an extent of 6–9% by the time the sucralose-6-benzoate content is maximized.

EXAMPLE 11

Reaction Profile of the Chlorination of Sucrose -6-Benzoate with Phosgene

Figure 6:
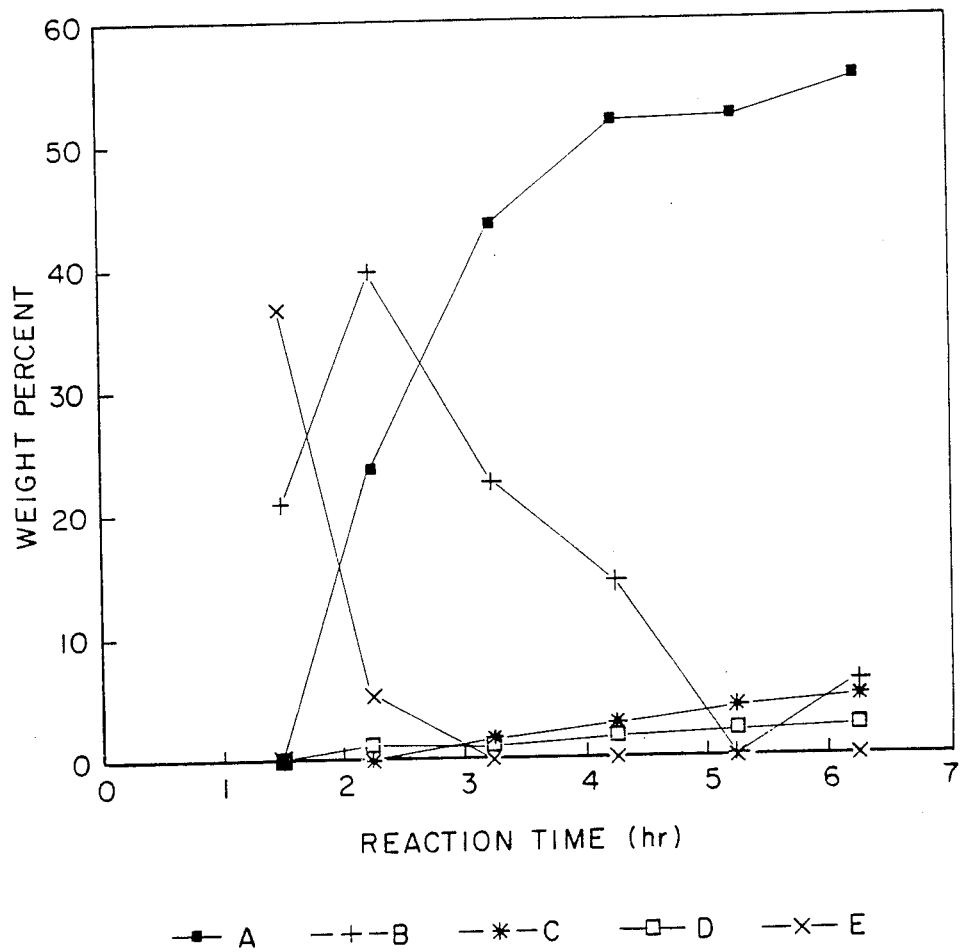
FIG. 6 is a graph of concentrations of the individual components of the reaction mixture of Example 11 versus time.
Figure 7:
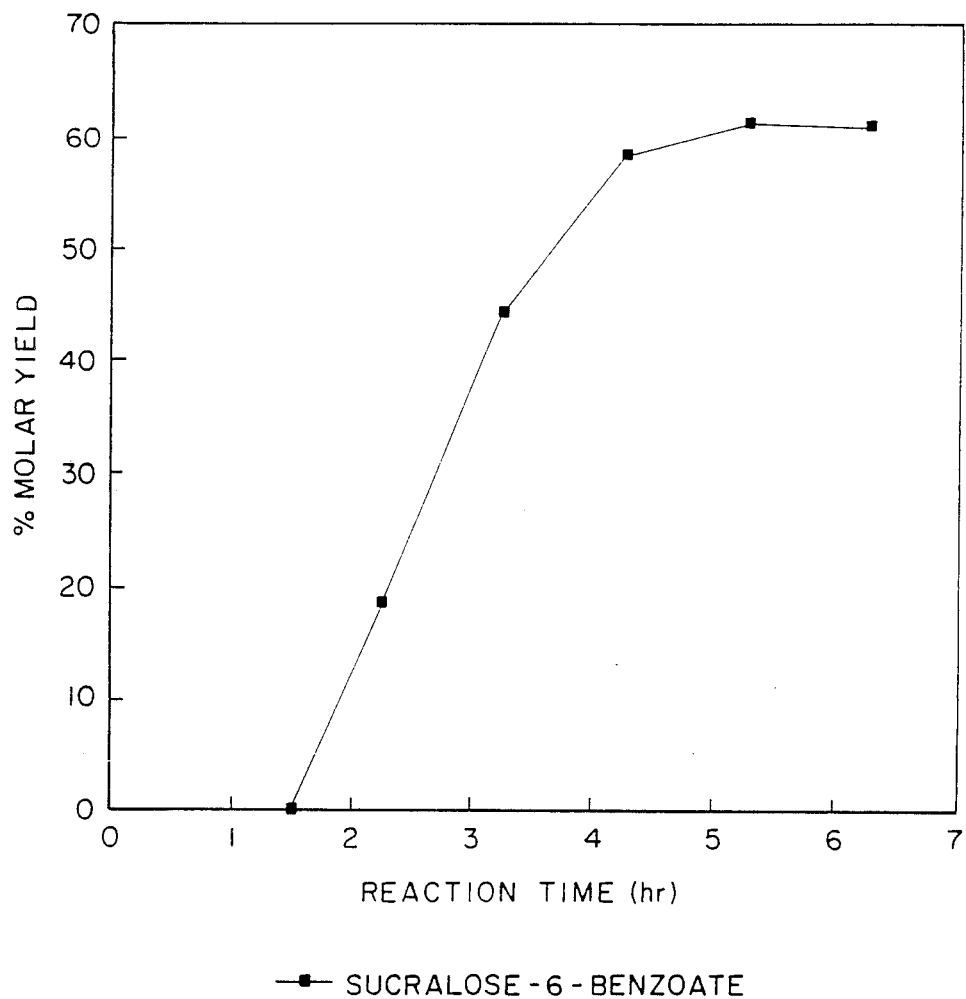
FIG. 7 is a graph of % molar yield of sucralose-6-benzoate versus reaction time for the reaction mixture of Example 11.

The formation of sucralose-6-benzoate as a function of time was followed by the reaction of 20.1 g of 98.1% sucrose-6-benzoate (19.7 g, 44.2 mmol) in 67 ml DMF with 62.1 g (0.628 mol) of phosgene and 165 ml DMF (preformed Vilsmeier-type salt). Aliquots of 35 ml were removed from the reaction mixture at various times, worked-up in the usual manner, and assayed for chlorosucrose derivatives as in the preceding Example. Reaction time was measured from the completion of addition of the sucrose-6-benzoate to the Vilsmeier-type salt mixture. The results are summarized in FIG. 6, wherein A represents sucralose-6-benzoate, B represents dichloro sucrose-6-benzoate, C represents tetrachloro sucrose-6-benzoate, D represents misellaneous trichloro sucrose-6-benzoates, and E represents monochloro sucrose-6-benzoate. Maximum sucralose-6-benzoate yields appear to be between 5 and 6 hours total reaction time, as is shown in FIG. 7.

EXAMPLE 12

Chlorination of Sucrose-6-Benzoate with Oxalyl Chloride

A 500-ml, four-neck, round-bottom flask, equipped with mechanical stirrer, thermometer, addition funnel, and reflux condenser topped with an argon inlet, was charged with 90 ml of DMF and cooled to −35° C. Oxalyl chloride (62.6 g, 43.0 ml, 0.493 mol) was added dropwise with vigorous stirring. During the oxalyl chloride addition the temperature of the reaction mixture increased from −35 ° C. to +7° C. with the cooling bath kept in place. Following the oxalyl chloride addition, 50 ml of DMF was added to facilitate stirring.

With continued cooling, the reaction mixture was treated dropwise between 10° C. and 15° C. with 20.1 g of 98.1% sucrose-6-benzoate (19.7 g, 44.0 mmol) in 50 ml of DMF. The reaction mixture, which contained light-yellow suspended solids, was heated over a period of about 15 min to 60° C. and held at this temperature for 15 min (homogeneous, golden-yellow). The solution was heated over about 15 min to 80° C. and held at this temperature for 60 min (reddish-orange). The mixture was then heated over about 15 min to 115° C. and held at this temperature for 3 hr (dark-red).

The reaction mixture was then cooled to about 5° C., and treated in one portion with 115 ml of ice-cold 4N NaOH (0.460 mol) with vigorous stirring. The temperature of the reaction mixture was 43° C. after the addition was complete, and the final pH was about 10. The reaction mixture was vigorously stirred for about 3 min, and then neutralized to about pH 7 by the addition of glacial acetic acid.

The crude product mixture was treated with 200 ml of ethyl acetate and stirred gently for several minutes. The layers were separated and the aqueous layer further extracted with ethyl acetate (3×100 ml). The organic extracts were combined, washed with water (2×100 ml), and treated with about 4 g of activated carbon for about 10 min at room temperature. The slurry was then filtered through Celite and the cake washed with ethyl acetate (2×50 ml).

The resulting clear-orange filtrate was evaporated to a syrup at 50° C. under water-aspirator vacuum. The syrup was treated with 50 ml of $H_2O$ and 50 ml of MTBE with thorough mixing at 50° C. This mixture was allowed to stand for about 72 hr and the product filtered, washed with MTBE (2×25 ml), and vacuum dried (50° C./24 hr/0.5 mm of Hg) to afford 14.3 g of pale-tan solid. HPLC showed the solid to consist of 90.8 wt % sucralose-6-benzoate (13.0 g, 25.9 mmol, 58.9% yield).

EXAMPLE 13

Chlorination of Sucrose-6-Benzoate with Thionyl Chloride

A 500-ml, four-neck, round-bottom flask, equipped with mechanical stirrer, thermometer, addition funnel, and reflux condenser topped with an argon inlet, was charged with 20.1 g of 98.1% sucrose-6-benzoate (19.7 g, 44.0 mmol) and 100 ml of DMF. This solution was cooled to −30° C. and treated dropwise over 10 min with 36.6 g (22.4 ml, 0.307 mol) of thionyl chloride. During the addition (−30° C. to −17° .) a very thick precipitate formed. The slurry became easier to stir as the temperature of the reaction mixture increased.

The reaction mixture was heated over a period of 15 min to 69° C. at which point the mixture was homogeneous. The solution was then heated to 100° C. over 45 min and held at this temperature for 60 min. The mixture was finally heated over 120 min to 113° C. and held at this temperature for 65 min.

The reaction mixture was cooled to −5° C. and treated in one portion with 70 ml of ice-cold 4N NaOH (0.280 mol) with vigorous stirring. The temperature of the reaction mixture was 35° C. after the addition was complete, and the final pH was about 9. The reaction mixture was vigorously stirred for several minutes and then neutralized with glacial acetic acid.

The crude product was treated with 150 ml of ethyl acetate and stirred gently for several minutes. The mixture was filtered through paper and the layers separated. The aqueous layer was further extracted with ethyl acetate (2×100 ml and 1×50 ml). The organic extracts were combined and treated with about 4.6 g of activated carbon for about 30 min at ambient temperature. The slurry was filtered through Celite and the cake washed with ethyl acetate.

The resulting filtrate was evaporated to a syrup under water-aspirator vacuum. The syrup was treated with 100 ml of $H_2O$ and 100 ml of MTBE, and allowed to stand overnight. The crystalline product was filtered, washed with large amounts of water and MTBE, and vacuum dried (50° C./18 hr/0.5 mm of Hg) to afford 8.79 g of off-white solid. HPLC analysis showed the product to contain 90.2 wt % sucralose-6-benzoate (7.93 g, 15.8 mmol, 35.9% yield). HPLC analysis showed an additional 3.04 g of sucralose-6-benzoate (6.06 mmol, 10.8% yield) to have been retained in the MTBE layer of the filtrate.

EXAMPLE 14

Chlorination of Sucrose -6-Benzoate with Elevated Temperature Phosgene Addition and Calcium Hydroxide Neutralization A 2000-ml, one-neck, round-bottom flask was charged with 42.7 g of 93.6% sucrose-6-benzoate (40.0 g, 89.7 mmol) and 500 ml of DMF. Approximately 350 ml of solvent was removed using a rotary evaporator (mechanical pump, 25° C. bath temperature). The benzoate solution was diluted to a total volume of 250 ml with DMF, and transferred to a 1000-ml, four-neck, round-bottom flask equipped with mechanical stirrer, thermometer, addition funnel topped with an argon inlet, and Dewar-type condenser filled with dry ice.

With ice-bath cooling, the reaction mixture was treated over 20 min with 97.7 g (69.8 ml, 987 mmol) of neat phosgene. During the course of the addition the temperature of the reaction rose from about 5° C. to about 50° C. The reaction was then heated over 30 min to 115° C., and held at this temperature for 4 hr.

After cooling to room temperature, the reaction mixture was transferred to a 2000-ml beaker equipped with overhead stirrer and cooling bath. The reaction mixture was cooled to 10° C. and treated in one portion with a slurry of 44.8 g (605 mmol) of $Ca(OH)_2$ in 400 ml of $H_2O$. The temperature rose to 49° C., and the final pH was 7. An additional small amount of solid $Ca(OH)_2$ was added to raise the pH to 9. The mixture was stirred at this pH for about 3 min, and then neutralized to about pH 7 by the addition of 5 ml of glacial acetic acid.

The stirred mixture was treated with 350 ml of ethyl acetate and about 20 g of activated carbon for 30 min at room temperature. After the addition of Celite, the mixture was filtered on a coarse-frit filter and the filter cake washed with ethyl acetate (2×150 ml). The layers were separated and the aqueous layer washed with ethyl acetate (150 ml).

The combined organic layers were washed with $H_2O$ (2×150 ml), brine (1×150 ml), and then evaporated to a syrup which weighed 38.94 g (rotary evaporator, mechanical pump, 50° C. bath temperature). The syrup was treated with 225 ml of 2:1 MTBE-$H_2O$ with rotation at 50° C. Crystallization rapidly occurred. The triphasic mixture was treated with 200 ml of 1:1 MTBE-$H_2O$, allowed to cool slowly with rotation over 30 min, and then allowed to stand overnight at ambient conditions.

The product was filtered on a coarse-frit filter, washed with 100 ml of $H_2O$ and 100 ml of MTBE, air-dried for 30 min, and then vacuum dried (0.8 mm of Hg/45° C./24hr). This provided 27.74 g of off-white solid shown by HPLC to contain 87.8 wt % sucralose-6-benzoate (24.36 g, 48.5 mmol, 54.1% yield).

EXAMPLE 15

Optional Recrystallization of Sucralose -6-Benzoate

A series of samples of sucralose-6-benzoate, of varying amounts and purities as indicated below, were combined to give a total weight of 300.9 g.

| COMBINED SUCRALOSE-6-BENZOATE SAMPLES | | | | |
|---|---|---|---|---|
| | ASSAY (Wt %) | | | |
| SAMPLE MASS (g) | SUCRALOSE-6-BENZOATE | DICHLORO S-6-B | TETRACHLORO S-6-B | IMPURITY-PROBABLE TETRACHLORO |
| 13.0 | 90.4 | 5.0 | 4.4 | 1.4 |
| 78.3 | 84.5 | 8.2 | 2.8 | 2.4 |
| 77.8 | 78.7 | 9.9 | 2.0 | — |
| 59.7 | 83.7 | 9.8 | 1.8 | 0.8 |
| 49.0 | 81.8 | 5.3 | 2.8 | — |
| 23.1 | 75.6 | 13.6 | 1.4 | 0.8 |
| 300.9 g | | | | |

The combined samples of sucralose-6-benzoate above were dissolved in 800 ml $CH_3OH$ at 60° C., but crystallized as a soldi mass on cooling. This was diluted with more methanol (500 ml) and water (250 ml) in order to facilitate filtration. Recovered solids were dried at 50 ° C. overnight to give 92.44 g (first crop).

The filtrate was diluted with 1.5 L of water and stirred at room temperature while more surcalose-6-benzoate crystallized. Solids recovered by filtration were dried as before to give 162 g (second crop).

A third crop (4.56 g) crystallized from the filtrate on standing overnight.

| | | ASSAY (%-wt) | |
|---|---|---|---|
| CROP | MASS (g) | SUCRALOSE-6-BENZOATE | DICHLORO'S | TETRACHLORO |
| 1 | 92.44 | 86.4 | 4.8 | 1.6 |
| 2 | 162.0 | 86.5 | 2.9 | 2.0 |
| 3 | 4.56 | 83.9 | 6.4 | 0.6 |

Recovery = 259.00 g (86.1%)

2. Second recrystallization. Sucralose--benzoate (259 g) was dissolved in 750 ml methanol at 40°-50° C., the solution was filtered; the residue and funnel rinsed with 250 ml methanol. The warm filtrate was diluted with 950 ml water at 60° C. (filtered) plus 250 ml water at room temperature. The warm filtrate was allowed to cool slowly and crystallize, while stirring overnight. The solid recovered by filtration was washed with water-methanol mixtures in proportions 1:1 (300 ml), 2:1 ml (300 ml) and 3:1 (300 ml) then vacuum dried at 50° C. overnight to give 231 g (89.2%) crystalline sucralose-6-benzoate.

| | ASSAY (%-wt) | |
|---|---|---|
| SUCRALOSE-6-BENZOATE | DICHLORO'S | TETRACHLORO |
| 100.6 | 1.2 | 1.4 |

3. Third recrystallization. The product was again dissolved in methanol (800 ml) at 60° C., filtered, and the filtrate diluted with 950 ml water at 60° C. The mixture cooled and crystallized overnight. Recovered solids (vacuum filtration) were washed with water-methanol 1:1 (400 ml) and 3:2 (500 ml) then dried at 50° C. overnight to give 212.7 g (92.1%) of sucraloses-6-benzoate.

| | ASSAY (%-wt) | |
|---|---|---|
| TOSBEN | DICHLORO'S | TETRACHLORO |
| 91.4* | N.D.** | 1.1 |

*(wet?)

**None detected.

EXAMPLE 16

Converstion of Recrystallized Sucralose -6-Benzoate to Sucralose

A 2000 ml, 4-neck, round-bottom flask, equipped with overhead stirrer, thermometer, drying tube, and stopper, was charged with 207.3 g of 91.4% sucralose-6-benzoate (377.64 mmol) and 1.0 L of methanol. The mixture was heated to dissolve the sucralose-6-benzoate, then cooled to 15° C. To the resulting solution was added in a single portion 25 ml of 0.84M potassium hydroxide in methanol (21 mmol KOH). The resulting solution was stirred at room temperature for 5 hours while monitoring the reaction progress periodically by TLC ($CHCl_3$-$CH_3OH$-Acetic acid; 4:0.85:0.15).

When complete, the reaction mixture was neutralized by addition of IRC-50 (H+) resin in portions while monitoring the pH (electrode). The neutral solution was filtered and the resin washed with 2×250 ml portions of methanol. The combined filtrates were evaporated to a soft foam (244.6 g).

The foam was dissolved in 1 L water and the aqueous solution extracted with 3×250 ml ethyl acetate to remove methyl benzoate, unreacted sucralose-6-benzoate, and other nonpolar impurities. The combined organic layers were concentrated to about 200 ml and back-extracted with 2×100 ml water to recover sucralose-6-benzoate. Extractions were monitored by TLC.

The combined aqueous layers were concentrated to a thick, light- brown solution (487 g; 29 wt % sucralose, corresponds to 94.0% crude yield) which was decolorized with ACTICARBONE for 25 min at room temperature. The mixture was filtered through a Celite pad and the pad washed with 600 ml $H_2O$. The combined filtrate was concentrated to a mass of 180.8 g at 70° C. Some sucralose had already crystallized from solution.

The mixture was allowed to cool gradually over 3.5-4 hrs to 40° C. then over 1.5 hrs to 10° C. to complete the crystallization. Product was recovered by vacuum filtration with the aid of recycled filtrate, the filter cake was thoroughly dewatered, rinsed with 20 ml cold water, air dried overnight, then transferred to a crystallizing dish and dried at 45°-50° C. for 5 hr to give 112.29 g (282.4 mmol) of sucralose (mp 119°-120° C., decomp.; $[\alpha_D^{20°} = +87.1°$ (C, 1.23, $H_2O$)). The colorless crystalline product had an HPLC purity of 99.6 wt %. The first crystalline crop obtained corresponds to 74.5% of the theoretical yield. The remaining mother liquors are saturated with sucralose and may be recycled into the crystallization of subsequent batches of sucralose.

EXAMPLE 17

Chlorination of Sucrose -6-Acetate with Phosgene

A solution of sucrose-6-acetate (43.56 mmol) in DMF (180 ml) was vacuum distilled (45° C.) in a 500-ml, 4-neck, round-bottom flask equipped with overhead stirrer, thermometer, and pressure equalizing funnel. When approximately 50 ml of distillate had been collected, the flask was vented to atmospheric pressure with argon, the mixture cooled to ambient temperature and the distillation equipment replaced with a cold-finger condenser.

The residue was further cooled to −25° C., the condenser charged with $CO_2$/acetone cooling mixture and $COCl_2$ (28.1 ml, 392 mmol) delivered to the addition funnel. $COCl_2$ was added dropwise to the solution over 25 min. When the addition was completed, the mixture was allowed to warm to room temperature then heated to 65° C. and held at this temperature for 30 min. The mixture was then heated gradually to 112°-114° C. and held there for 4.5 hrs.

The mixture was cooled to 10° C. and quenched by the addition of cold 4M $NH_4OH$ (100 ml). The temperature of the mixture rose quickly to 60° C. then cooled to 45° C. and was then neutralized with 2-3ml glacial acetic acid. Sucralose-6-acetate was extracted with ethyl acetate (7×100 ml), the extract decolorized with carbon and evaporated to a thick syrup (19 g). The syrup was dissolved in water (23 ml) at 40° C. then left to cool and crystallize overnight.

The product was recovered by vacuum filtration and dried (9.1 g, 76.2%-wt). A further 2.54 g crystallized from the mother liquor to give a total yield of sucralose-6-acetate of about 46%.

What is claimed is:

1. A process for the chlorination of sucrose-6-esters to produce 6', 4,1'-trichloro-sucrose-6-esters which comprises the steps of:
   (a) adding at least seven molar equivalents of an acid chloride to a reaction mixture containing a sucrose-6-ester and a tertiary amide to form a chloroformiminium chloride salt in the presence of said sucrose-6-ester, whereby the chloroformiminium salt forms an O-alkylformiminium chloride adduct with the hydroxyl groups of the sucrose-6-ester;
   (b) subjecting the reaction mixture product of step (a) to an elevated temperature not higher than about 85° C. for a period of time sufficient to produce a mixture of chlorinated sucrose-6-ester products consisting essentially of monochlorosucrose-6-ester, 4,6'-dichlorosucrose-6-ester, and 1',6'-dichlorosucrose-6-ester; and
   (c) subjecting the reaction mixture product of step (b) to an elevated temperature of at least about 100° C. but not higher than about 130° C. for a period of time sufficient to produce a chlorinated product comprising predominanly 1',4,6'-trichlorosucrose-6-ester.

2. The process of claim 1 wherein said tertiary amide contains an N-formyl group.

3. The process of claim 2 wherein said tertiary amide is N,N-dimethylformamide.

4. The process of claim 1 wherein the acid chloride is phosgene.

5. The process of claim 2 wherein the acid chloride is phosgene.

6. The process of claim 3 wherein the acid chloride is phosgene.

7. The process of claim 1 which includes the step of neutralizing the reaction mixture produced by step (c) with aqueous alkali to regenerate the hydroxyl groups at positions 2, 3, 3', and 4' of the trichlorinated sucrose-6-ester product.

8. The process of claim 2 which includes the step of neutralizing the reaction mixture produced by step (c) with aqueous alkali to regenerate the hydroxyl groups at positions 2, 3, 3', and 4' of the trichlorinated sucrose-6-ester product.

9. The process of claim 3 which includes the step of neutralizing the reaction mixture produced by step (c) with aqueous alkali to regenerate the hydroxyl groups at positions 2, 3, 3', and 4' of the trichlorinated sucrose-6-ester product.

10. The process of claim 1 wherein the product of step (c) is recovered by extraction with an organic solvent that is a solvent for the 6',4,1'-trichloro sucrose-6-ester product of step (c) but is a non-solvent for di-chloro- and mono-chloro-sucrose-6-esters.

11. The process of claim 2 wherein the product of step (c) is recovered by extraction with an organic solvent that is a solvent for the 6',4,1'-trichloro sucrose-6-ester product of step (c) but is a non-solvent for di-chloro- and mono-chloro-sucrose-6-esters.

12. The process of claim 3 wherein the product of step (c) is recovered by extraction with an organic solvent that is a solvent for the 6',4,1'-trichloro sucrose-6-ester product of step (c) but is a non-solvent for di-chloro- and mono-chloro-sucrose-6-esters.

13. The process of claim 10 wherein the organic solvent is methyl tert-butyl ether or ethyl acetate.

14. The process of claim 11 wherein the organic solvent is methyl tert-butyl ether or ethyl acetate.

15. The process of claim 12 wherein the organic solvent is methyl tert-butyl ether or ethyl acetate.

16. The process of claim 1 wherein the sucrose-6-ester is sucrose-6-benzoate or sucrose-6-acetate.

17. The process of claim 2 wherein the sucrose-6-ester is sucrose-6-benzoate or sucrose-6-acetate.

18. The process of claim 3 wherein the sucrose-6-ester is sucrose-6-benzoate or sucrose-6-acetate.

19. The process of claim 4 wherein the sucrose-6-ester is sucrose-6-benzoate or sucrose-6-acetate.

20. The process of claim 5 wherein the sucrose-6-ester is sucrose-6-benzoate or sucrose-6-acetate.

21. The process of claim 6 wherein the sucrose-6-ester is sucrose-6-benzoate or sucrose-6-acetate.

22. The process of claim 10 which includes the step of neutralizing the reaction mixture produced by step (c) with aqueous alkali to regenerate the hydroxyl groups at positions 2, 3, 3', and 4' of the trichlorinated sucrose-6-ester product.

23. The process of claim 11 which includes the step of neutralizing the reaction mixture produced by step (c) with aqueous alkali to regenerate the hydroxyl groups at positions 2, 3, 3',and 4' of the trichlorinated sucrose-6-ester product.

24. The process of claim 12 which includes the step of neutralizing the reaction mixture produced by step (c) with aqueous alkali to regenerate the hydroxyl groups at positions 2, 3, 3', and 4' of the trichlorinated sucrose-6-ester product.

* * * * *

UNITED STATES PATENT AND TRADEMARK OFFICE
CERTIFICATE OF CORRECTION

PATENT NO. : 4,980,463

DATED : December 25, 1990

INVENTOR(S) : Robert E. Walkup et al.

It is certified that error appears in the above-identified patent and that said Letters Patent is hereby corrected as shown below:

Claim 1, column 22, line 41: "predominanly" should be --predominantly--.

Signed and Sealed this

Fifteenth Day of September, 1992

Attest:

DOUGLAS B. COMER

Attesting Officer

Acting Commissioner of Patents and Trademarks